United States Patent
Rankin, Sr.

(10) Patent No.: US 12,345,509 B2
(45) Date of Patent: *Jul. 1, 2025

(54) NON-LETHAL DEFENSIVE FLUID COMPOSITION AND PRESSURIZED DELIVERY SYSTEM

(71) Applicant: David Daniel Rankin, Sr., Yadkinville, NC (US)

(72) Inventor: David Daniel Rankin, Sr., Yadkinville, NC (US)

(73) Assignee: David D. Rankin, Sr., Yadkinville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/432,876

(22) Filed: Feb. 5, 2024

(65) Prior Publication Data

US 2024/0230283 A1 Jul. 11, 2024

Related U.S. Application Data

(60) Continuation of application No. 18/137,134, filed on Apr. 20, 2023, now Pat. No. 11,920,907, which is a
(Continued)

(51) Int. Cl.
*F41H 9/10* (2006.01)
*A61K 31/085* (2006.01)
(Continued)

(52) U.S. Cl.
CPC ............. *F41H 9/10* (2013.01); *A61K 31/085* (2013.01); *A61K 31/194* (2013.01); *A61K 31/69* (2013.01);
(Continued)

(58) Field of Classification Search
CPC ............ F41H 9/10; F41H 9/00; A61K 31/085; A61K 31/194; A61K 31/69; A61K 35/02;
(Continued)

(56) References Cited

U.S. PATENT DOCUMENTS

| 4,670,179 A | 6/1987 | Inamorato et al. |
| 5,217,708 A | 6/1993 | Pinkney |

(Continued)

FOREIGN PATENT DOCUMENTS

| EP | 0106692 A1 | 4/1984 |
| EP | 1674133 A1 | 6/2006 |

(Continued)

OTHER PUBLICATIONS

Planet Ingredients, 2018; www.planetinc.com/ingredients.htm (Year: 2018).

(Continued)

*Primary Examiner* — Cephia D Toomer
(74) *Attorney, Agent, or Firm* — Shumaker, Loop & Kendrick, LLP

(57) ABSTRACT

A lubric gel composition for personal defense includes a fatty acid at a concentration ranging from 5 wt % to 10 wt % of the composition, a thickening agent at a concentration ranging from 1.75 wt % to 8.75 wt % of the composition, a detergent at a concentration ranging from 1.03 wt % to 4.07 wt % of the composition, a surfactant at a concentration ranging from 2 wt % to 15 wt % of the composition, and water at a concentration ranging from 66 wt % to 90.21 wt % of the composition.

9 Claims, 2 Drawing Sheets

Related U.S. Application Data continuation of application No. 17/727,119, filed on Apr. 22, 2022, now Pat. No. 11,650,030, which is a division of application No. 16/830,362, filed on Mar. 26, 2020, now Pat. No. 11,320,245, which is a continuation-in-part of application No. 16/509,830, filed on Jul. 12, 2019, now abandoned.

(60) Provisional application No. 62/760,612, filed on Nov. 13, 2018.

(51) Int. Cl.
| | | |
|---|---|---|
| *A61K 31/194* | (2006.01) | |
| *A61K 31/69* | (2006.01) | |
| *A61K 35/02* | (2015.01) | |
| *A61K 47/10* | (2017.01) | |
| *A61K 47/12* | (2006.01) | |
| *A61K 47/20* | (2006.01) | |
| *A61K 47/34* | (2017.01) | |
| *A61K 47/36* | (2006.01) | |
| *A61K 47/38* | (2006.01) | |
| *C10M 105/24* | (2006.01) | |

(52) U.S. Cl.
CPC .............. *A61K 35/02* (2013.01); *A61K 47/10* (2013.01); *A61K 47/12* (2013.01); *A61K 47/20* (2013.01); *A61K 47/34* (2013.01); *A61K 47/36* (2013.01); *A61K 47/38* (2013.01); *C10M 105/24* (2013.01)

(58) Field of Classification Search
CPC ........ A61K 47/10; A61K 47/12; A61K 47/20; A61K 47/34; A61K 47/36; A61K 47/38; C10M 105/24
See application file for complete search history.

(56) References Cited

U.S. PATENT DOCUMENTS

| | | | |
|---|---|---|---|
| 5,653,970 | A | 8/1997 | Vermeer |
| 6,903,064 | B1 | 6/2005 | Kasturi et al. |
| 11,320,245 | B2 | 5/2022 | Rankin, Sr. |
| 11,650,030 | B2 * | 5/2023 | Rankin, Sr. ............ A61K 47/34 508/179 |
| 11,662,182 | B2 | 5/2023 | Rankin, Sr. |
| 11,920,906 | B2 | 3/2024 | Rankin, Sr. |
| 2003/0017018 | A1 | 9/2003 | Bahary |
| 2006/0054634 | A1 | 3/2006 | Mekata |
| 2006/0130246 | A1 | 6/2006 | Molenda et al. |
| 2006/0240054 | A1 | 10/2006 | Graney et al. |
| 2009/0095494 | A1 | 4/2009 | Cordani |
| 2015/0203795 | A1 | 7/2015 | Miracle et al. |
| 2017/0087199 | A1 | 3/2017 | Patron et al. |
| 2020/0148965 | A1 | 5/2020 | Rankin, Sr. |
| 2022/0244023 | A1 | 8/2022 | Rankin, Sr. |
| 2022/0244024 | A1 | 8/2022 | Rankin, Sr. |
| 2023/0258435 | A1 | 8/2023 | Rankin, Sr. |
| 2023/0258436 | A1 | 8/2023 | Rankin, Sr. |

FOREIGN PATENT DOCUMENTS

| | | |
|---|---|---|
| JP | H-0625987 U | 4/1994 |
| RU | 2562993 C1 | 9/2015 |
| WO | 2006055640 A2 | 5/2006 |
| WO | 2006091561 A1 | 8/2006 |
| WO | 2007120547 A1 | 10/2007 |
| WO | 2009004390 A2 | 1/2009 |

OTHER PUBLICATIONS

European Search Report for EP Application No. 20210809.8 dated May 27, 2021 (8 pages).

International Search Report for PCT/US2019/056449 mailed Jan. 10, 2020 (9 pages).

International Preliminary Report on Patentability for PCT/US2019/056449 mailed May 27, 2021 (8 pages).

Notice of Allowance (NOA) issued for U.S. Appl. No. 17/727,119, mailed Jan. 9, 2023 (7 pages).

Non-Final Office Action i(NFOA) ssued for U.S. Appl. No. 17/727,119, mailed Nov. 23, 2022 (6 pages).

Non-Final Office Action (NFOA) issued for U.S. Appl. No. 17/727,112, mailed Dec. 20, 2022 (7 pages).

Notice of Allowance (NOA) issued for U.S. Appl. No. 17/727,112, mailed Jan. 23, 2023 (7 pages).

Supplementary European Search Report for EP Patent Application No. 19884365.8 dated Aug. 4, 2022 (9 pages).

Non-Final Office Action (NFOA) issued for U.S. Appl. No. 18/432,813, mailed Sep. 10, 2024 (7 pages).

\* cited by examiner

NON-LETHAL DEFENSIVE FLUID COMPOSITION AND PRESSURIZED DELIVERY SYSTEM

TECHNICAL FIELD AND BACKGROUND OF THE INVENTION

This invention relates to a defensive fluid and pressurized delivery system for use by individuals, in classrooms, for crowd control, in commercial environments, and for firefighting. Specifically this invention relates to a defensive fluid chemical composition having high lubricity and a gel-like consistency. In one embodiment, the product is formulated to temporarily impair vision, but not to cause pain or stinging to the eyes. In an alternative embodiment, the product is formulated to temporarily impair vision, and to cause temporary stinging to the eyes. Each will have utility in different situations.

In recent years, safety and security has become a top priority for the public in light of tragic events such as mass shootings, home invasions, and rioting. Numerous proposals of how the public can be protected and protect themselves have been discussed on a national and international scale. Many of the solutions to date, such as weapons and pepper spray, are not viable for various reasons.

One solution is for individuals to carry guns for protection. However, guns are not always accessible to the general public. Additionally, guns are often subject to bans in many locations such as schools, private businesses, and public spaces. Another problem is the training and experience required for the safe use and care of guns.

Pepper spray, chemical Mace®, tear gas, and other types of lachrymator agents are frequently used in crowd control and carried as personal protection. The basic idea is that the composition causes extreme irritation and/or inflammation to the target's eyes such that an assailant is disabled. While these methods have had success, many states and schools consider these personal defense sprays to be weapons and have added heavy regulation or outright banned the sale. Schools have generally banned students from carrying these types of sprays. Even in situations where these spray products are permissible, the use of these sprays which inflame or irritate the eyes of an assailant are only effective in close proximity to the assailant where the nose, mouth or eyes can be targeted. This greatly reduces the time for a targeted individual to escape.

There is a need for a product and pressurized delivery system that can be used as a personal defense spray and pre-emptively delay or disable an assailant, increasing the time for an targeted individual to escape.

There is also a need for a product and pressurized delivery system that has specific eye-irritating characteristics that dissipate without long term damage to the eyes.

SUMMARY OF THE INVENTION

It is therefore an aspect of the present invention to provide a defensive fluid composition that disables or delays an assailant and can be applied pre-emptively to a surface.

It is another aspect of the invention to provide a defensive fluid composition which increases the lubricity of a surface.

It is another aspect of the invention to provide a defensive fluid composition delivery system that can be installed in walls and ceilings.

It is another aspect of the invention to provide a defensive fluid composition that is biodegradable, non-toxic, water soluble, non-corrosive, and non-explosive.

It is another aspect of the invention to provide a defensive fluid composition that does not sting the eyes.

It is another aspect of the invention to provide a defensive fluid that causes temporary stinging to the eyes.

In all aspects of the invention the defensive fluid is intended to have temporary effect with no injury to the eyes.

These and other objects and advantages of the present invention are achieved in one preferred embodiment set forth below by providing a lubric gel composition for personal defense which includes a fatty acid at a concentration ranging from 5 wt % to 10 wt % of the composition, a thickening agent at a concentration ranging from 1.75 wt % to 8.75 wt % of the composition, a detergent at a concentration ranging from 1.03 wt % to 4.07 wt % of the composition, a surfactant at a concentration ranging from 2 wt % to 15 wt % of the composition, and water at a concentration ranging from 66 wt % to 90.21 wt % of the composition.

According to another embedment of the invention, the lubric gel composition includes a preservative at a concentration ranging from 0.01 wt % to 1.00 wt % of the composition.

According to another embodiment of the invention, preservative includes sodium benzoate.

According to another embodiment of the invention, the fatty acid includes glycerine.

According to another embodiment of the invention, the thickening agent includes guar gum at a concentration ranging from 1 wt % to 5 wt % of the composition.

According to another embodiment of the invention, the thickening agent includes methyl cellulose at a concentration ranging from 0.75 wt % to 3.75 wt % of the composition.

According to another embodiment of the invention, the detergent includes sodium lauryl sulfate at a concentration ranging from 1 wt % to 4 wt % of the composition.

According to another embodiment of the invention, the detergent includes sodium dioctyl sulfosuccinate at a concentration ranging from 0.03 wt % to 0.07 wt % of the composition.

According to another embodiment of the invention, the surfactant includes a non-ionic, anionic, and/or an amphoteric surfactant.

According to another embodiment of the invention, the surfactant includes an amphoteric surfactant at a concentration ranging from 2 wt % to 40 wt % of the surfactant.

According to another embodiment of the invention, the amphoteric surfactant includes coco amino propionate.

According to another embodiment of the invention, the water is deionized water.

According to another embodiment of the invention, an additive is selected from the group essentially consisting of: a dye, a luminescent, and a phosphorescent.

According to another embodiment of the invention, a bag-on-valve spray canister is adapted to contain and spray the composition.

According to another embodiment of the invention, a pressurized composition delivery system is provided which includes a pressurized reservoir containing the composition and having a fluid outlet through which the composition can flow. A valve is connected to the fluid outlet of the reservoir having a closed position preventing flow of composition out of the reservoir and an open position enabling the composition to flow. A sprinkler head is adapted to receive and spray the composition when the valve is open.

According to another embodiment of the invention, a lubric gel composition for personal defense is provided which includes glycerin at a concentration ranging from 5 wt % to 10 wt % of the composition. Guar gum is included at a concentration ranging from 1 wt % to 5 wt % of the composition. Sodium benzoate is included at a concentration ranging from 0.01 wt % to 1 wt % of the composition. Methyl cellulose is included at a concentration ranging from 0.75 wt % to 3.75 wt % of the composition. Sodium lauryl sulfate is included at a concentration ranging from 1 wt % to 4 wt % of the composition. Sodium dioctyl sulfosuccinate is included at a concentration ranging from 0.03 wt % to 0.07 wt % of the composition. A surfactant is included which has a non-ionic surfactant, a anionic surfactant, and/or an amphoteric surfactant at a concentration ranging from 2 wt % to 15 wt % of the composition. Deionized water is included at a concentration ranging from 66 wt % to 90.21 wt % of the composition.

According to another embodiment of the invention, a lubric gel composition for personal defense, comprising, Propylene Glycol @ 0.1 wt % to 10 wt %, Citric acid @ 5 wt % to 20 wt %; Trihydroxyborane @ 0.1 wt % to 5 wt %; Pumicite @ 0.1% to 5 wt %; Sodium chloride @ 5 wt % to 20% wt; Cocoamide DEA @ 0.1 wt % to 5 wt %; and Phenoxyenthanol @ .025 wt % to 1 wt %.

According to another embodiment of the invention, the lubric gel includes Polyvinyl Alcohol 1.0-5%.

According to another embodiment of the invention, the lubric gel includes Boric Acid at 0.125-1 wt %.

According to another embodiment of the invention, a pressurized lubric gel composition delivery system for personal defense is provided which has a pressurized reservoir containing the composition and having a fluid outlet through which the composition can flow. A valve is connected to the fluid outlet of the reservoir having a closed position preventing flow of composition out of the reservoir and an open position enabling flow of composition out of the reservoir. A sprinkler head is adapted to receive and spray the composition when the valve is open.

According to another embodiment of the invention, a trigger is positioned remote from the delivery system and connected to the valve by a wire or by wireless technology whereby activating the trigger opens the valve.

According to another embodiment of the invention, a refilling system is provided which has a fluid inlet on the reservoir through which the composition can flow. A valve is connected to the fluid inlet adapted to prevent the flow of composition out of the reservoir through the fluid inlet. A refilling fitting is connected to the valve and adapted to receive composition for refilling the reservoir. A pressure gauge is connected to the reservoir to monitor pressure within the reservoir.

According to another embodiment of the invention, the sprinkler head is positioned on a wall or ceiling or a building.

BRIEF DESCRIPTION OF THE DRAWINGS

The present invention is best understood when the following detailed description of the invention is read with reference to the accompanying drawings, in which.

DETAILED DESCRIPTION OF THE PREFERRED EMBODIMENT

Figure 1:
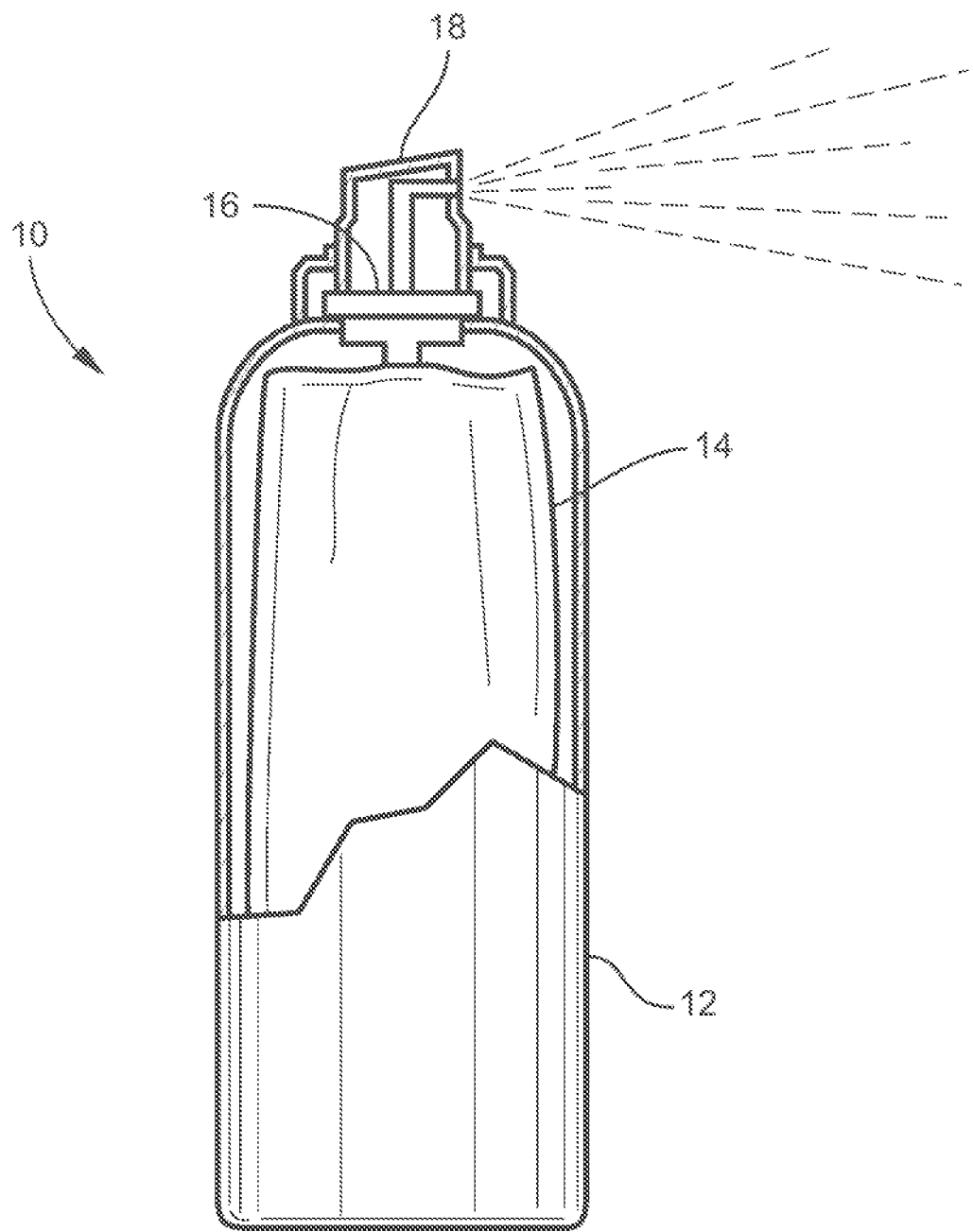
FIG. 1 is a partial cutaway of a hand-held pressurized composition delivery system.

A lubric gel composition which can be applied to various surfaces for personal defense and a pressurized lubric gel composition delivery system is described. It is envisioned that the composition may be sprayed onto a wide variety of surfaces such as concrete, tile, and wood or sprayed directly at an individual. When applied to surfaces such as a walking surface the composition creates a slick surface for the purposes of disabling or delaying an individual. A coating of the composition on an individual's hands increases difficulty of manipulating items such as weapons and doorknobs. The composition maintains a gel-like consistency when stored, sprayed, or coating a surface and does not foam in its natural state. This gel-like quality is important for maintaining the lubricity of the composition.

In addition to the primary purpose of increasing lubricity of a surface, the composition also has secondary features such as fire suppression/extinguishing and contact irritation of eyes/nose/mouth. Protective eyewear having a coat of the composition will smear when wiped and reduce visibility. The composition is also environmentally friendly, non-toxic, non-corrosive, non-lethal, and easily washable off surfaces.

Primary components of one preferred composition designed not to sting the eyes include a fatty acid, a thickening agent, a detergent, a surfactant, and water. Optionally, a preservative may be included. Other additives are envisioned such as dyes, illuminates, and/or phosphorescent which leave a detectable signature on any individuals who came into contact with the defensive fluid. Each of the components may include multiple substances, or one substance may function as two of the components. The water is preferably deionized water at a concentration ranging from 66 wt % to 90.21 wt % of the overall solution.

A pre-mix is prepared which contains the fatty acid and the thickening agent. The fatty acid is preferably at a concentration ranging from 5 wt % to 10 wt % of the overall composition. The fatty acid coats the thickening agent to reduce clumping when exposed to water. The fatty acid also acts as a barrier film on hard surfaces and enhances lubricity. In one embodiment of the invention, the fatty acid is glycerin.

The thickening agent serves to increase the film strength and enhance lubricity. The thickening agent is preferably at a concentration ranging from 1.95 wt % to 13.75 wt % of the overall composition. In one embodiment of the invention guar gum, methyl cellulose, and polyethylene oxide are included in the overall composition as thickening agents. Guar gum is preferably at a concentration ranging from 1 wt % to 5 wt % of the overall composition and methyl cellulose is preferably at a concentration ranging from 0.75 wt % to 3.75 wt % of the overall composition. Polyethylene oxide is preferably at a concentration ranging from 0.2 wt % to 10 wt % of the composition.

The detergent serves as a wetting agent to ensure the surface is wetted and can potentially enhance lubricity. The detergent is preferably at a concentration ranging from 1.03 wt % to 4.07 wt % of the overall composition. In one embodiment of the invention the detergent includes of sodium laurel sulfate and sodium dioctyl sulfosuccinate. Sodium laurel sulfate is preferably at a concentration ranging from 1 wt % to 4 wt % of the overall composition and sodium dioctyl sulfosuccinate is preferably at a concentration ranging from 0.03 wt % to 0.07 wt % of the overall composition.

The surfactant serves to slow the rate of evaporation and provide enhanced lubricity. The surfactant is preferably at a concentration ranging from 2 wt % to 15 wt % of the overall concentration. In one embodiment, the surfactant comprises a non-ionic surfactant, an anionic surfactant, and an amphoteric surfactant. The amphoteric surfactant is coco amino propionate and is preferably at a concentration ranging from 2 wt % to 40 wt % of the surfactant.

A preservative may be added to the composition in order to increase longevity or self-life of the composition. The preservative is preferably at a concentration ranging from 0.01 wt % to 1.00 wt % of the overall composition. In one embodiment the preservative is sodium benzoate.

In the above formulation, a make-up diluent such as water is used to arrive at a total of 100 percent.

In accordance with another embodiment of the invention, a lubric gel composition which can be applied to various surfaces for personal defense and is intended to temporarily incapacitate an individual by impairing vision and causing a temporary stinging or burning sensation, without causing injury. A pressurized lubric gel composition delivery system includes Propylenel Glyco @ 0.1 wt % to 10 wt %; Citric acid @ 0.1 wt % to 5 wt %; Trihydroxyborane @ 0.1 wt % to 5 wt %, Pumicite @ 0.1% to 5 wt % and Sodium chloride @ 0.1 wt % to 10% wt; Cocoamide DEA @ 0.1 wt % to 5 wt % and Phenoxyenthanol @ 0.025 wt % to 1 wt.

In accordance with yet another embodiment of the invention, a lubric gel composition which can be applied to various surfaces for personal defense and is intended to temporarily incapacitate an individual by impairing vision and causing a temporary stinging or burning sensation, without causing injury. A pressurized lubric gel composition delivery system includes Propylene Glycol @ 0.1 wt % to 10 wt %; Citric acid @ 5 wt % to 20 wt %; Trihydroxyborane @ 0.1 wt % to 5 wt %, Pumicite @ 0.1% to 5 wt % and Sodium chloride @ 5 wt % TO 20% wt; Cocoamide DEA @ 0.1 wt % to 5 wt % and Phenoxyenthanol @ 0.025 wt % to 1 wt.

In a further embodiment, the composition may also include Polyvinyl Alcohol 1.0-5% and/or Boric Acid 0.125-1%.

These compositions causes temporary moderate to severe eye irritation, and reduces the ability for the eyes to open due to the irritation and gumminess of the solution.

Delivery of the composition may be accomplished by hand-held spray devices of various sizes depending on the specific application. Small capacity devices, such as a four ounce device, can be carried by an individual on a daily basis for self-defense. Larger capacity devices, for example eight to twenty ounce devices, can be stored in a manner similar to the storage of fire extinguishers in homes, classrooms, school and business entryways, commercial buildings, and other locations where people frequent. Other applications are envisioned such as bulk delivery by vehicles such as tankers or airplanes.

Referring now to FIG. 1, a pressurized hand-held composition delivery device 10 is shown. The hand-held device 10 utilizes 'bag-on-valve' technology. A pressurized canister 12 contains a bag 14 which holds the composition. The hand-held device 10 is operated by engaging a trigger 18 which cooperates with a valve 16 to spray the composition.

The hand-held device 10 is able to spray the composition in streams of twenty feet or more with precision. Other applications where the composition would be applied, such as utility poles before/during parades or riots may be performed with other spray devices having varying strength of spray, width of spray, and shape of spray depending on the application. Other portable delivery systems are envisioned such as conventional spray bottles.

Figure 2:
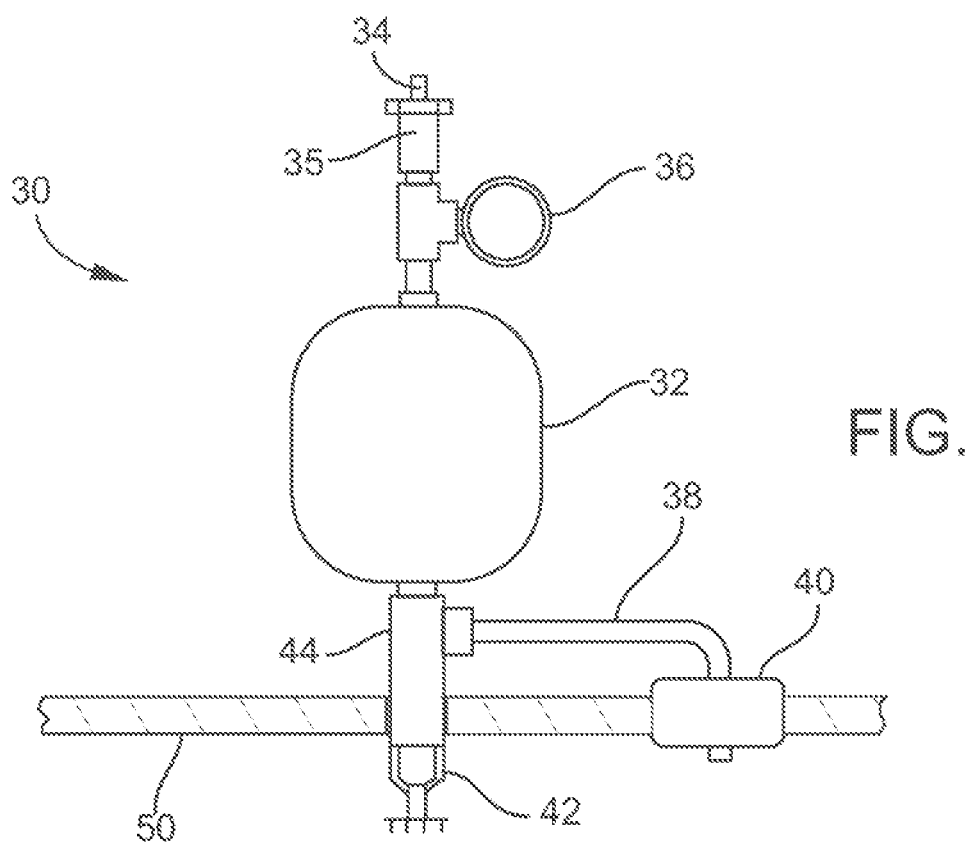
FIG. 2 is a schematic view of a pressurized composition delivery system installed on a ceiling.
Figure 3:
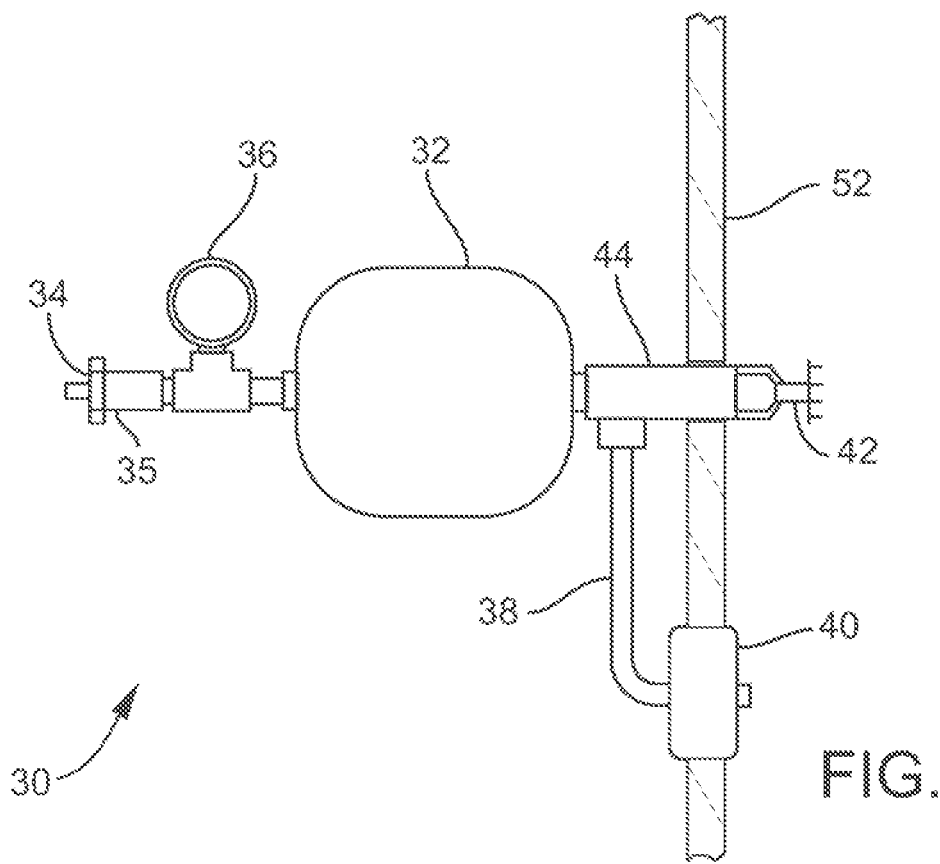
FIG. 3 is a schematic view of a pressurized composition delivery system installed on a wall.

FIGS. 2 and 3 show a pressurized composition delivery system 30 where the delivery system 30 is installed in a ceiling 50 or a wall 52 respectively. This delivery system 30 has a pressurized reservoir 32 containing the composition. A switch 40 is connected to a valve 44 such as a solenoid valve which controls flow of the composition out of the reservoir 32 and into a sprinkler head 42. Wires travel from the switch 40 to the valve 44 through a conduit 38. When the switch 40 is activated, the valve 44 opens and allows the composition to flow into the sprinkler head 42 and spray outward from the ceiling 50 or wall 52.

The composition, which is sprayed from a ceiling 50 or a wall 52, can serve multiple functions. The sprayed defensive fluid will coat the surface of the floor, creating a slick/slippery floor. In an emergency situation, a slippery floor can slow down and possibly deter an assailant, giving others more time to run and/or hide. The additional fire extinguishing feature of the defensive fluid allows for the spray to be used on fires. It is also envisioned that existing fire systems can be retrofitted to accommodate the composition.

Pressure on the delivery system 30 is monitored by a pressure gauge 36 connected to the reservoir 32. When the pressure is low, or after the delivery system 30 has been emptied of the composition, the reservoir 32 has a refill fitting 34 that can be used to refill the delivery system 30. The refill fitting 34 may be similar to conventional air fittings. A one-way check valve 35 is positioned between the refill fitting 34 and the reservoir 32 to prevent backflow. In other embodiments the emptied reservoir 32 can be replaced with a full reservoir 32 instead of being refilled.

This delivery system 30 may be installed in ceilings 50 in a similar manner as fire sprinkler systems such that the switch 40 is located in an accessible location and only the sprinkler head 42 protrudes through the ceiling 50. Similarly, the delivery system 30 can be installed in a wall 52 where the sprinkler head 42 protrudes from the wall 52. Sprinkler heads 42 can be angled for maximum effectiveness in each application.

Other configurations are also envisioned where the delivery system 30 has multiple sprinkler heads 42 per reservoir 32 or where a single switch 40 controls multiple valves 44 and reservoirs 32. Plumbing, such as pipes, can be used to connect the reservoir 32 to the valve 44 and connect the valve 44 to the sprinkler head 42.

Switches 40 can be simple buttons, switches similar to light switches, or pull stations similar to fire alarms. They can also be encased to prevent accidental activation. Since the switch 40 is connected by wires, it can be located anywhere that can be hard wired. The wires can be in long conduits 38 or added to pre-existing building wiring. In lieu of hard wiring the valve 44 can be controlled by wireless technology when the switch 40 is activated.

A lubric gel composition and pressurized delivery system according to the invention have been described with reference to specific embodiments and examples. Various details of the invention may be changed without departing from the scope of the invention. Furthermore, the foregoing description of the preferred embodiments of the invention and best mode for practicing the invention are provided for the purpose of illustration only and not for the purpose of limitation, the invention being defined by the claims.

I claim:

1. A personal defense composition, comprising:
   (a) Propylene Glycol ranging from 0.1 wt % to 10 wt % of the overall composition;

(b) Citric acid ranging from 5 wt % to 20 wt % of the overall composition;
(c) Trihydroxyborane ranging from 0.1 wt % to 5 wt % of the overall composition;
(d) Pumicite ranging from 0.1 wt % to 5 wt % of the overall composition;
(e) Sodium chloride ranging from 5 wt % to 20 wt % of the overall composition;
(f) Cocoamide DEA ranging from 0.1 wt % to 5 wt % of the overall composition; and
(g) Phenoxyethanol ranging from 0.025 wt % to 1 wt % of the overall composition.

2. The composition of claim 1, further comprising Polyvinyl Alcohol.

3. The composition of claim 1, further comprising Boric Acid.

4. The composition of claim 2, further comprising Boric Acid.

5. The composition of claim 1, further comprising water.

6. The composition of claim 5, wherein the water ranges from 34 wt % to 89.575 wt % of the overall composition.

7. The composition of claim 2, wherein the composition comprises from 1.0 wt % to 5 wt % of the overall composition Polyvinyl Alcohol.

8. The composition of claim 3, wherein the composition comprises from 0.125 wt % to 1 wt % of the overall composition Boric Acid.

9. The composition of claim 7, wherein the composition comprises from 0.125 wt % to 1 wt % of the overall composition Boric Acid.

* * * * *